(12) United States Patent
Fisher et al.

(10) Patent No.: US 10,784,877 B2
(45) Date of Patent: Sep. 22, 2020

(54) EXTENDED PERIOD TIMER CIRCUITS FOR OPHTHALMIC DEVICES

(71) Applicant: Johnson & Johnson Vision Care, Inc., Jacksonville, FL (US)

(72) Inventors: Gregory James Fisher, Indialantic, FL (US); Donald Scott Langford, Melbourne Beach, FL (US); Randall B. Pugh, St. Johns, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 751 days.

(21) Appl. No.: 15/386,044

(22) Filed: Dec. 21, 2016

(65) Prior Publication Data

US 2018/0175870 A1    Jun. 21, 2018

(51) Int. Cl.
| | | |
|---|---|---|
| *A61M 35/00* | (2006.01) | |
| *H03L 7/183* | (2006.01) | |
| *G02C 7/04* | (2006.01) | |
| *G02C 11/00* | (2006.01) | |
| *A61F 9/00* | (2006.01) | |
| *A61F 9/007* | (2006.01) | |
| *H03K 23/40* | (2006.01) | |

(52) U.S. Cl.
CPC ............ *H03L 7/183* (2013.01); *A61F 9/0008* (2013.01); *A61F 9/0017* (2013.01); *A61F 9/00772* (2013.01); *G02C 7/04* (2013.01); *G02C 11/10* (2013.01); *H03K 23/40* (2013.01); *A61F 2250/008* (2013.01); *A61F 2250/0067* (2013.01)

(58) Field of Classification Search
CPC .... H03L 7/183; A61F 9/0017; A61F 9/00772; A61F 2250/0067; A61F 2250/008; G02C 7/04; G02C 11/10
USPC ...................................................... 604/294
See application file for complete search history.

(56) References Cited

U.S. PATENT DOCUMENTS

| | | | |
|---|---|---|---|
| 5,592 | A | 5/1848 | Brooman |
| 902,472 | A | 10/1908 | Cole |
| 2011/0215875 | A1* | 9/2011 | Yagishita ............... H03L 7/00 331/34 |
| 2013/0226110 | A1 | 8/2013 | Pugh et al. |
| 2013/0258275 | A1* | 10/2013 | Toner ..................... G02C 7/04 351/159.03 |
| 2015/0065905 | A1 | 3/2015 | Pugh |

FOREIGN PATENT DOCUMENTS

EP    2772791 A1    9/2014

OTHER PUBLICATIONS

PCT Search Report Application No. PCT/US2017/067810 dated Aug. 7, 2018.

* cited by examiner

*Primary Examiner* — Andrew J Mensh

(57) ABSTRACT

Programmable timer circuits are disclosed. One timer circuit may include a reference circuit configured to generate a bias current, a current controlled oscillator configured to receive the bias current c, and a frequency divider network configured to divide an output of the oscillator. The timer circuit may be capable of timing for 24 hour period, while using less than 5nA of quiescent current.

12 Claims, 12 Drawing Sheets

EXTENDED PERIOD TIMER CIRCUITS FOR OPHTHALMIC DEVICES

BACKGROUND OF THE DISCLOSURE

1. Field of the Disclosure

The present disclosure relates to timer circuits and more particularly, to ophthalmic devices, such as wearable lenses, including contact lenses, punctal plugs, implantable lenses, including intraocular lenses (IOLs) and any other type of device comprising ocular components that incorporate the timer circuits.

2. Discussion of the Related Art

Ophthalmic devices may be utilized to correct myopia, hyperopia, astigmatism as well as other visual acuity defects. Ophthalmic devices may also be utilized to enhance the natural appearance of the wearer's eyes. As a non-limiting example, contact lenses or "contacts" are simply lenses placed on the anterior surface of the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality, such as administration of active agents, as is explained herein.

Active agents are frequently administered to the eye for the treatment of ocular diseases and disorders. Conventional means for delivering active agents to the eye involve topical application to the surface of the eye. The eye is uniquely suited to topical administration because, when properly constituted, topically applied active agents can provide lubrication and/or penetrate through the cornea and rise to therapeutic concentration levels inside the eye. Active agents for ocular diseases and disorders may be administered orally or by injection, but such administration routes can be disadvantageous in that, in oral administration, the active agent may reach the eye in too low a concentration to have the desired pharmacological effect, and their use can be complicated by significant, systemic side effects and injections pose the risk of infection.

The majority of ocular active agents and/or lubricants are currently delivered topically using eye drops which, though effective for some applications, can be inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Therefore, sometimes one or more drops miss the eye. Older patients may have additional problems instilling drops due to arthritis, unsteadiness, and decreased vision. Pediatric and psychiatric patient populations pose difficulties as well.

Prior topical sustained release systems include gradual release formulations, either in solution or ointment form, which are applied to the eye in the same manner as eye drops but less frequently. Such formulations are disclosed, for example, in U.S. Pat. No. 3,826,258 issued to Abraham and U.S. Pat. No. 4,923,699 issued to Kaufman. Due to their method of application, however, these formulations result in many of the same problems detailed above for conventional eye drops. In the case of ointment preparations, additional problems are encountered such as a blurring effect on vision and the discomfort of the sticky sensation caused by the thick ointment base.

Alternately sustained release systems have been configured to be placed into the conjunctival cul-de-sac, between the lower lid and the eye. Such units typically contain core drug-containing containment cells surrounded by a hydrophobic copolymer membrane which controls the diffusion of the drug. Examples of such devices are disclosed in U.S. Pat. No. 3,618,604 issued to Ness, U.S. Pat. No. 3,626,940 issued to Zaffaroni, U.S. Pat. No. 3,845,770 issued to Theeuwes et al., U.S. Pat. No. 3,962,414 issued to Michaels, U.S. Pat. No. 3,993,071 issued to Higuchi et al., and U.S. Pat. No. 4,014,335 issued to Arnold. However, due to their positioning, the units may be uncomfortable and poor patient acceptance is again encountered. Moreover, leakage of the active agent should be prevented when some active agents are used. Specifically, when administering active agents, the effectiveness of the active agent may be compromised when the active agent receptors are exposed to them continuously.

Other methods similarly allow for the eluting of an active agent, e.g., medicament and/or a lubricant, over a period of time. Again, some active agents however can be most efficacious when periodically delivered in a predetermined dosed amount or at a time of need. In one approach seeking to provide delivery of an active agent at pre-determined times, a containment device with multi-layer reservoir cap structure has been described in U.S. Pat. No. 8,211,092, issued to Uhland et al. This system however uses an electrical current to rupture, i.e., melt or vaporize, a reservoir's cap using the heat generated by the electrical current. Although the described delivery system may be suitable for the delivery of an active agent in some environments, this system would generally not be suitable for use in sensitive organs or environments, including, for example, an ophthalmic environment, due to the flash and heat generated during rupture of the cap which can damage surrounding cells. Further, the described system may also not be suitable in a sensitive organ or environment as the rupture will produce debris that can damage or bother the surrounding organ or environment. In an ophthalmic environment, for example, the debris may detrimentally affect the vision of a user.

Accordingly, alternative methods, systems, and devices for delivering medicaments to an ophthalmic area may be beneficial especially if discrete dosage amounts may be delivered over significant periods of time in a way that is innocuous to the user.

Energy consumption, or more particularly current consumption, for such devices is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption after potentially remaining idle for years. Accordingly, there exists a need for devices and systems that are optimized for low-cost, long-term reliable service, safety and size while providing the required power.

SUMMARY OF THE DISCLOSURE

The present disclosure relates to programmable timer circuits. Timer circuit may include a reference circuit configured to generate a bias current, a current controlled oscillator configured to receive the bias current, and a frequency divider network configured to divide an output of the oscillator. The timer circuit may be capable of timing for 24 hour period, while using less than 5 nA of quiescent current. The present disclosure relates to ophthalmic devices that may comprise the programmable timer circuits. Ophthalmic devices may comprise a contact lens, an intraocular lens, an overlay lens, an ocular insert, or an optical insert, or a combination thereof. The ophthalmic devices may further comprise one or more containment cells, wherein at least one of the one or more containment cells contains an active agent, and wherein the at least one of the one or more containment cells is configured to release the active agent in response to an output of the timer signal. In certain aspects, an alarm may be triggered in response to at least the timer signal. The alarm may be one or more of audible, optical, and haptic.

Circuits and devices of the present disclosure may comprise a reference circuit configured to generate a bias current. A current controlled oscillator configured to receive the bias current. A frequency divider network configured to divide an output of the oscillator, wherein the bias current is generated based at least on the divided output of the oscillator. The circuits may be configured to generate a timer signal over a period of time of at least 12 hours, while using less than 5 nA of quiescent current. The timer signal may be based at least on the divided output of the oscillator.

BRIEF DESCRIPTION OF THE DRAWINGS

The foregoing and other features and advantages of the disclosure will be apparent from the following, more particular description of preferred embodiments of the disclosure, as illustrated in the accompanying drawings.

DETAILED DESCRIPTION OF THE PREFERRED EMBODIMENTS

Figure 1:
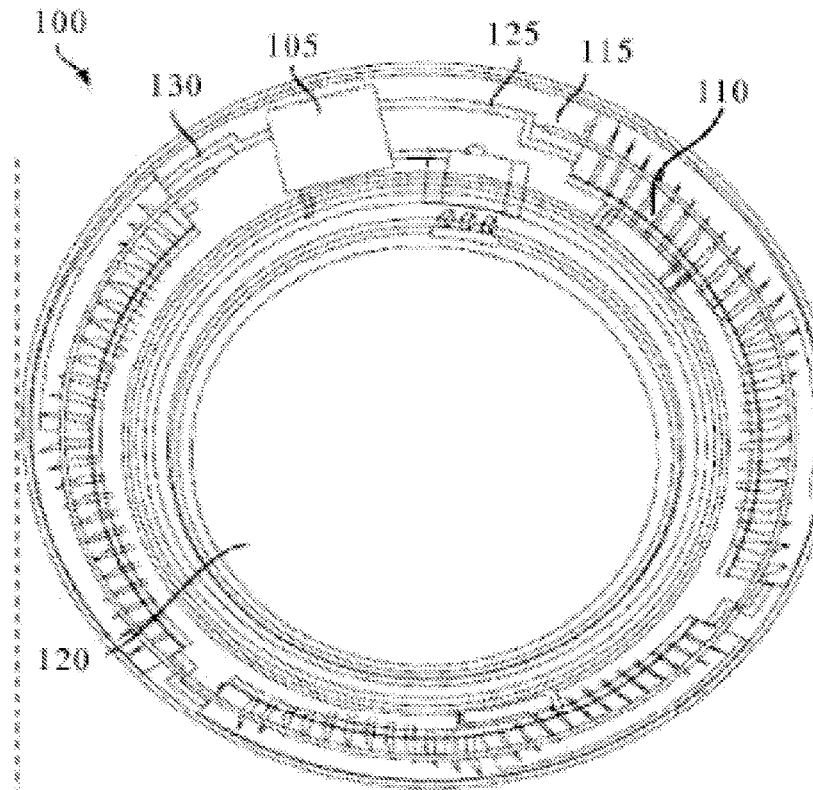
FIG. 1 is a diagrammatic representation of the top view of a media insert that may be included as part of an ophthalmic device including both optics and the active agent release system in accordance with aspects of the present disclosure.

In the past few decades, ophthalmic lenses have been improved to help treat conditions of dry eye, among others. More recently they have gained attention for use as drug delivery systems for the treatment of ocular diseases and conditions. However, as previously mentioned, several challenges exist with formulating a drug to release at the desired daily rate and/or dose that will give efficacy while limiting adverse events. According to some aspects of the present disclosure, an alternative or supplementary release strategy can involve the use of energized micro-electronics to control and enact the innocuous delivery of individual dose amounts at pre-determined times, upon demand and/or upon a sensed condition.

Unlike diffusion based delivery systems, which are characterized by a release rate which is dependent on the active agent diffusing through an inert water insoluble membrane barrier, the present disclosure can allow for delivery of an active agent upon demand, addressing shortcomings of diffusion based drug delivery and leaking. For example, there are two basic diffusion designs: reservoir devices and matrix devices. Reservoir devices are those in which a core of drug is surrounded by a polymeric membrane. The nature of the membrane determines the rate of release of drug from the system and there is often leakage throughout. The process of diffusion is generally described by a series of equations governed by Fick's first law of diffusion. A matrix device typically consists of a drug dispersed homogenously throughout a polymer. Both of these provide constant exposure by a tissue surface which may include the receptors to the active agent, e.g., a drug. By exposing tissue constantly to the active agent, the efficacy of the active agent can decrease over time, and in some events, prevent the active agent from having the intended effect completely.

Accordingly, reservoir and matrix drug delivery systems are considered diffusion based sustained release systems and constitute any dosage form that provides continuous medication over a period of time, often an extended period of time. The intended goal of a sustained release system is to maintain therapeutic levels of a drug for an extended period and this is usually accomplished by attempting to obtain zero-order release from the sustained release system. Sustained release systems generally do not attain this type of release profile but try to approximate it by releasing in a slow first-order manner. Over time, however, the drug release rate from reservoir and matrix sustained release systems will decay and become non therapeutic.

Recent developments in ophthalmic devices including, for example, contact lenses, have occurred enabling functionalized ophthalmic devices that can be energized. The energized ophthalmic device can include the necessary elements to correct and/or enhance the vision of users using embedded micro-electronics. Additional functionality using micro-electronics can include, for example, variable vision correction, tear fluid analysis, audio, and/or visual feedback to the user. According to some aspects of the present disclosure, an ophthalmic device that can include an active agent release system that can be capable of releasing an active agent to the ophthalmic environment of a user, upon demand, at a pre-determined time, and/or upon a sensed condition, is provided. The release can be generally innocuous to the user or in some embodiments allow for simple participation by the user. For example, one or more active agent(s) may be contained in one or more containment cells until an activation element is engaged. In some embodiments, a processor forming part of the active agent release system can be in wireless communication with one or more device(s) and receive signal data that can be used for the release of the active agent. The device(s) can include, for example, a smart phone, a tablet, a personal computer, a remote transmitter (e.g., a fob, MP3 player, or PDA), and a medical drug delivery device (e.g., a drug pump), and the like.

Timing elements may be or comprise a time reference block or a timer circuit, such as illustrated and described below. Certain timer circuits may be configured as a long period timer (e.g., on the order of 24 hours) and may be low power (<5 nA of quiescent current) during the period. As an example, timer circuits may be configured on or in an ophthalmic device or other ocular drug delivery device that may be located in the Caruncula or other region of the eye. As a further example, the various systems described herein may make use of the timer circuits such as indication systems, alarms, and the like that may be configured to alert a user of a time-sensitive or time-dependent event. As such, a timer circuit may need to provide a reliable time signal over an extended period of time such as over 12 hours, 18 hours, or 24 hours, for example. The timer circuit may also need to provide such a time signal, while minimizing usage of electrical current and thus maximizing power management.

Glossary

In this description and claims directed to the disclosed disclosure, various terms may be used for which the following definitions will apply:

Energized: as used herein refers to the state of being able to supply electrical current to or to have electrical energy stored within.

Energy: as used herein refers to the capacity of a physical system to do work. Many uses within this disclosure may relate to the said capacity being able to perform electrical actions in doing work.

Energy Source: as used herein refers to a device or layer that is capable of supplying Energy or placing a logical or electrical device in an Energized state.

Energy Harvester: as used herein refers to a device capable of extracting energy from the environment and converting it to electrical energy.

Functionalized: as used herein refers to making a layer or device able to perform a function including for example, energization, activation, or control.

Leakage: as used herein refers to unwanted loss of energy.

Ophthalmic Device: as used herein refers to any device that resides in or on the eye. These devices may provide optical correction, may be cosmetic, or may provide functionality unrelated to the eye. For example, the term lens may refer to a contact lens, intraocular lens, overlay lens, ocular insert, optical insert, or other similar device through which vision is corrected or modified, or through which eye physiology is cosmetically enhanced (e.g. iris color) without impeding vision. Alternatively, the Lens may provide non-optic functions such as, for example, monitoring glucose, delivering sound signals and/or administrating medicine. In some embodiments, the preferred lenses of the disclosure are soft contact lenses are made from silicone elastomers or hydrogels, which include, for example, silicone hydrogels, and fluorohydrogels.

Lithium Ion Cell: as used herein refers to an electrochemical cell where Lithium ions move through the cell to generate electrical energy. This electrochemical cell, typically called a battery, may be reenergized or recharged in its typical forms.

Media Insert: as used herein refers to an encapsulated insert that will be included in an energized ophthalmic device. The energization elements and circuitry may be incorporated in the Media Insert. The Media Insert defines the primary purpose of the energized ophthalmic device. For example, in embodiments where the energized ophthalmic device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose, sound delivery, and/or administering medicine.

Operating Mode: as used herein refers to a high current draw state where the current over a circuit allows the device to perform its primary energized function.

Optical Zone: as used herein refers to an area of an ophthalmic lens through which a wearer of the ophthalmic lens sees.

Power: as used herein refers to work done or energy transferred per unit of time.

Rechargeable or Re-energizable: as used herein refers to a capability of being restored to a state with higher capacity to do work. Many uses within this disclosure may relate to the capability of being restored with the ability to flow electrical current at a certain rate and for a certain, reestablished period.

Reenergize or Recharge: as used herein refers to restoring to a state with higher capacity to do work. Many uses within this disclosure may relate to restoring a device to the capability to flow electrical current at a certain rate and for a certain, reestablished period.

Reference: as use herein refers to a circuit which produces an, ideally, fixed and stable voltage or current output suitable for use in other circuits. A reference may be derived from a bandgap, may be compensated for temperature, supply, and process variation, and may be tailored specifically to a particular application-specific integrated circuit (ASIC).

Reset Function: as used herein refers to a self-triggering algorithmic mechanism to set a circuit to a specific predetermined state, including, for example, logic state or an energization state. A Reset Function may include, for example, a power-on reset circuit, which may work in conjunction with the Switching Mechanism to ensure proper initialization of the chip, both on initial connection to the power source and on wakeup from Storage Mode.

Sleep Mode or Standby Mode: as used herein refers to a low current draw state of an energized device after the Switching Mechanism has been closed that allows for energy conservation when Operating Mode is not required.

Stacked: as used herein means to place at least two component layers in proximity to each other such that at least a portion of one surface of one of the layers contacts a first surface of a second layer. In some embodiments, a film, whether for adhesion or other functions may reside between the two layers that are in contact with each other through said film.

Stacked Integrated Component Devices or SIC Devices: as used herein refers to the products of packaging technologies that assemble thin layers of substrates that may contain electrical and electromechanical devices into operative-integrated devices by means of stacking at least a portion of each layer upon each other. The layers may comprise component devices of various types, materials, shapes, and sizes. Furthermore, the layers may be made of various device production technologies to fit and assume various contours.

Storage Mode: as used herein refers to a state of a system comprising electronic components where a power source is supplying or is required to supply a minimal designed load current. This term is not interchangeable with Standby Mode.

Substrate Insert: as used herein refers to a formable or rigid substrate capable of supporting an Energy Source within an ophthalmic lens. In some embodiments, the Substrate insert also supports one or more components.

Switching Mechanism: as used herein refers to a component integrated with the circuit providing various levels of resistance that may be responsive to an outside stimulus, which is independent of the ophthalmic device.

Recent developments in Ophthalmic Devices including, for example, contact lenses, have occurred enabling Functionalized Ophthalmic Devices that can be Energized. The Energized Ophthalmic Device can comprise the necessary elements to correct and/or enhance the vision of users using embedded micro-electronics. Additional functionality using micro-electronics can include, for example, variable vision correction, tear fluid analysis, and/or visual and/or audio feedback to the user.

Referring now to FIG. 1, a diagrammatic representation of the top view of a media insert that may be included as part of an exemplary ophthalmic device including both optics and an active agent release system is depicted. In particular, FIG. 1A shows a top view of an exemplary media insert 100 for an energized ophthalmic device 150 (shown in FIG. 1B) that includes the active agent release system 105. In some embodiments, the media insert 100 includes an optical zone 120 that may or may not be functional to provide vision correction. In embodiments where the energized function of the ophthalmic device is unrelated to vision, the optic zone 120 of the media insert 100 may be void of material. The media insert 100 can include a portion outside of the optical zone 120 including a substrate 115 incorporated with energization elements 110 connected to electronic components, including the active agent release system 105, by a series of interconnects, e.g., 125 and 130. In alternative embodiments, some electronic components may be included in the optical zone without detrimentally affecting the overall intended optical properties of the ophthalmic device. In such embodiments, for example, the electronic components may have translucent properties, be located in the center, or be small enough to not impact the overall intended optical effect.

Figure 2:
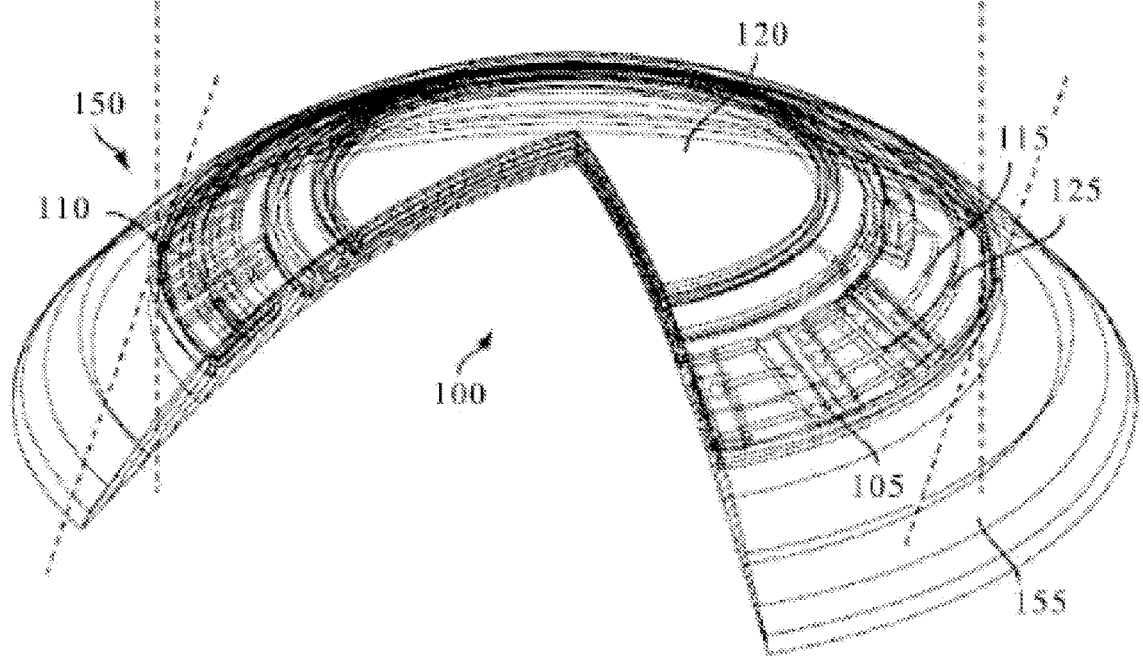
FIG. 2 is a diagrammatic representation of an isometric view of an ophthalmic device including the media insert depicted in FIG. 1A including both optics and the active agent release system in accordance with aspects of the present disclosure.

Referring now to FIG. 2, a diagrammatic cross section representation of an energized ophthalmic device 150 with the media insert 100 including both optics and the active agent release system 105 of FIG. 1A is depicted. According to some aspects of the present disclosure, the ophthalmic device 150 may be a contact lens designed to rest on the anterior surface of a patient's eye. For example, ophthalmic device 150 may include a soft hydrogel skirt 155 which can include a silicone-containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably include polymerizable functional groups such as acrylate, methacrylate, acrylamide, methacrylamide, vinyl, N-vinyl lactam, N-vinylamide, and styryl functional groups.

The functionalized media insert 100 can be partially or entirely embedded in the hydrogel portion 155; or in some embodiments the functionalized media insert 100 can be placed onto the hydrogel portion. In some embodiments, the media insert 100 can be used to encapsulate and act as a substrate for electronic elements and, in some embodiments, energization elements. In some embodiments, the electronic elements, including for example the active agent release system 105, can preferably be located outside of the optical zone 120, such that the device does not interfere with a user's sight. The active agent delivery system 105 may be powered through an external means, energy harvesters, and/or energization elements contained in the ophthalmic device 150. For example, in some embodiments the power may be received using an antenna (not shown) receiving RF signals that is in communication with the active agent release system 105.

Figure 3:
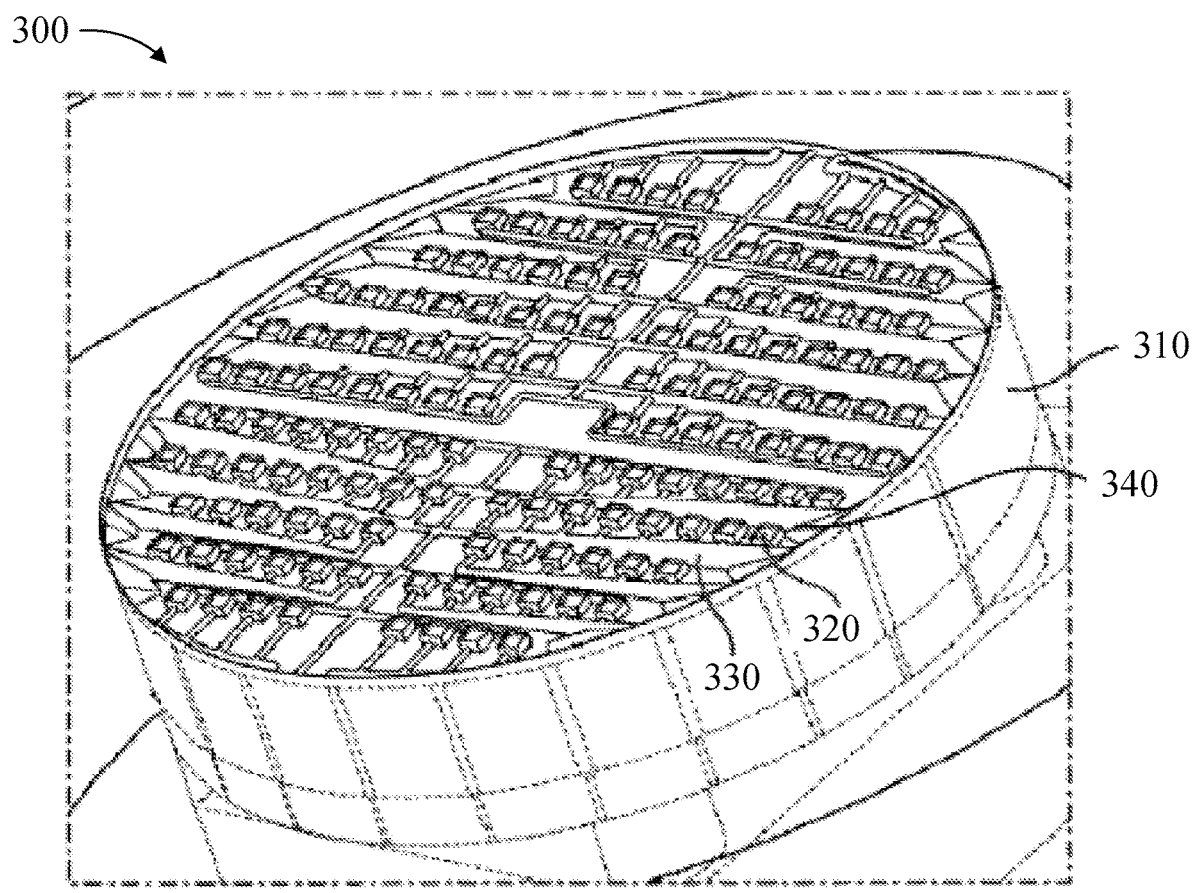
FIG. 3 is a close up representation of active agent release features in an energized containment array that may be incorporated in an ophthalmic device in accordance with aspects of the present disclosure.

Referring now to FIG. 3, a close up representation of a surface of semiconductor device 310 with the containment array 300 of containment cells 320 forming part of the active agent release system 105 is depicted. The semiconductor device 310, e.g., silicon piece, can include circuitry for the control of the containment array 300 and to ensure that each containment cell can be engaged by an activation element 340 to cause the dispensing of an active agent. Each containment cell can be a reservoir-shaped region of the silicon, and may be filled with the active agent, e.g., one or more of a lubricant, a saline, a solvent, a pharmaceutical, and a nutraceutical, during assembly. Interconnect metallurgy may be used to define a matrix of regions overlying at least of portion of a surface of each of the containment cells. The interconnect metallurgy can be located on the same side of the silicon as the circuits. Containment cell 320 can include a metal cap bonded in a manner such that it is under stress and contains the active agent. The metal cap can include one or more biocompatible metals including, for example, gold, titanium, nickel, stainless steel, cobalt-chromium, and nitinol. Other biocompatible non-permeable metals including binary metals may be used. According to some aspects of the disclosure, through the bonding of the metal cap to the silicon, by means of how it is assembled or the binary shape material, the metal cap can remain under stress while it is bonded. The assembly and bonding of the metal cap to the silicon piece may include, for example, braiding, welding, gluing, and the like.

The activation element 340 can include interconnects 330 positioned to be configured in such a manner that current flow may be directed to a portion or across the metal cap under stress on demand. This current flow and the stress which the metal cap is under can cause the metal cap to fold, thereby exposing the active agent to the surrounding environment. The folding can allow innocuous delivery of the active agent since, unlike some other systems, the metal does not have to melt or evaporate to expose the underlying contents of the containment cell. In some embodiments, the cap is manufactured so that the metal cap folds towards the inside of the containment cell. This can further prevent the metal cap from interfering with the surrounding cells and may assist ensuring that the active agent is dispensed accordingly. In other embodiments, the metal cap may be small enough that the folding does not produce an adverse effect to the surrounding cells and the direction of the folding does not affect the surrounding cells.

Figure 4:
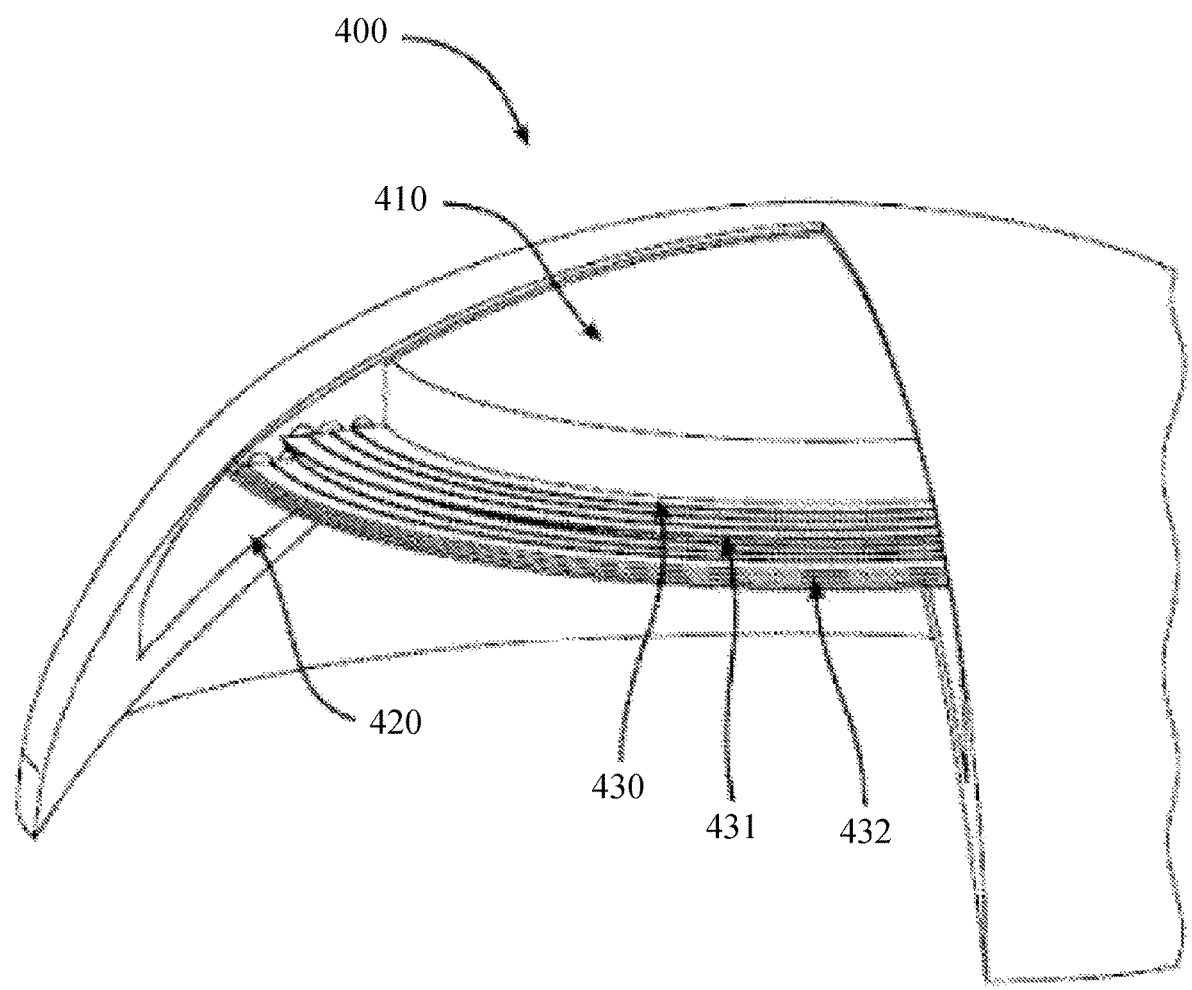
FIG. 4 is a schematic diagram of an exemplary cross section of stacked die integrated components implementing the active agent release system in accordance with aspects of the present disclosure.

Referring now to FIG. 4, a diagrammatic representation of another exemplary energized ophthalmic device including both optics and the active agent release system is depicted. In particular, a three dimensional cross section representation of an exemplary ophthalmic lens 400 including a functionalized layer media insert 420 configured to include the active agent release system on one or more of its layers 430, 431, 432, is illustrated. In some embodiments, the media insert 420 surrounds the entire periphery of the optical zone 410 of the ophthalmic lens 400. Media insert 420 may be in the form of a full annular ring, a partial annular ring, or other shapes that still may reside inside or on the hydrogel portion of the ophthalmic lens 400 and be within the size and geometry constraints presented by the ophthalmic environment of the user.

Layers 430, 431, and 432 illustrate three of the numerous layers that may be found in an exemplary media insert 420 including a stack of functional layers. In some embodiments, for example, a single layer may include one or more of: active and passive components and portions with structural, electrical or physical properties conducive to a particular purpose, including the communication system functions described herein. Furthermore, in some embodiments, a layer 430 may include an energy source, such as, one or more of: a battery, a capacitor, and a receiver within the layer 430. Layer 431 then, in a non-limiting exemplary sense, may include microcircuitry in a layer that detects actuation signals for the ophthalmic lens 400 or other ophthalmic device. In some embodiments, a power regulation layer 432, may be included that is capable of receiving power from external sources, charges the battery layer 430 and controls the use of battery power from layer 430 when the ophthalmic lens 400 is not in a charging environment. The power regulation may also control signals to an exemplary active lens, demonstrated as item 410 in the center annular cutout of the media insert 420.

An energized lens with an embedded media insert 420 may include an energy source, such as an electrochemical cell or battery as the storage means for the energy and in some embodiments, encapsulation, and isolation of the materials including the energy source from an environment into which an ophthalmic device is placed. In some embodiments, a media insert 420 can also include a pattern of circuitry, components, and energy sources. Various embodiments may include the media insert 420 locating the pattern of circuitry, components and energy sources around a periphery of an optic zone through which a wearer of an ophthalmic lens would see, while other embodiments may include a pattern of circuitry, components, and energy sources which can be small enough to not adversely affect the sight of the ophthalmic lens wearer and therefore the media insert 420 may locate them within, or exterior to, an optical zone.

Reference has been made to electronic circuits making up part of the componentry of ophthalmic devices incorporating the active agent release system. In some embodiments according to some aspects of the disclosure, a single and/or multiple discrete electronic devices may be included as discrete chips, for example, inside, on, or positioned near the media insert. In other embodiments, the energized electronic elements can be included in the media insert in the form of stacked integrated components. Such active agent release system may be activated based on a timer signal, as described herein. The timer signal may need to be referenced over extended periods of time while the ophthalmic device is in use. In particular, the timer circuits described herein may be configured to provide a timer signal over a period of time that is greater than 12 hours, greater than 13 hours, greater than 14 hours, greater than 15 hours, greater than 16 hours, greater than 17 hours, greater than 18 hours, greater than 19 hours, greater than 20 hours, greater than 21 hours, greater than 22 hours, greater than 23 hours, greater than 24 hours, and/or between 12 and 24 hours, including intervening end points. The time signal may also be made available during this time period while using a current of less than 5 nA of current.

Figure 5:
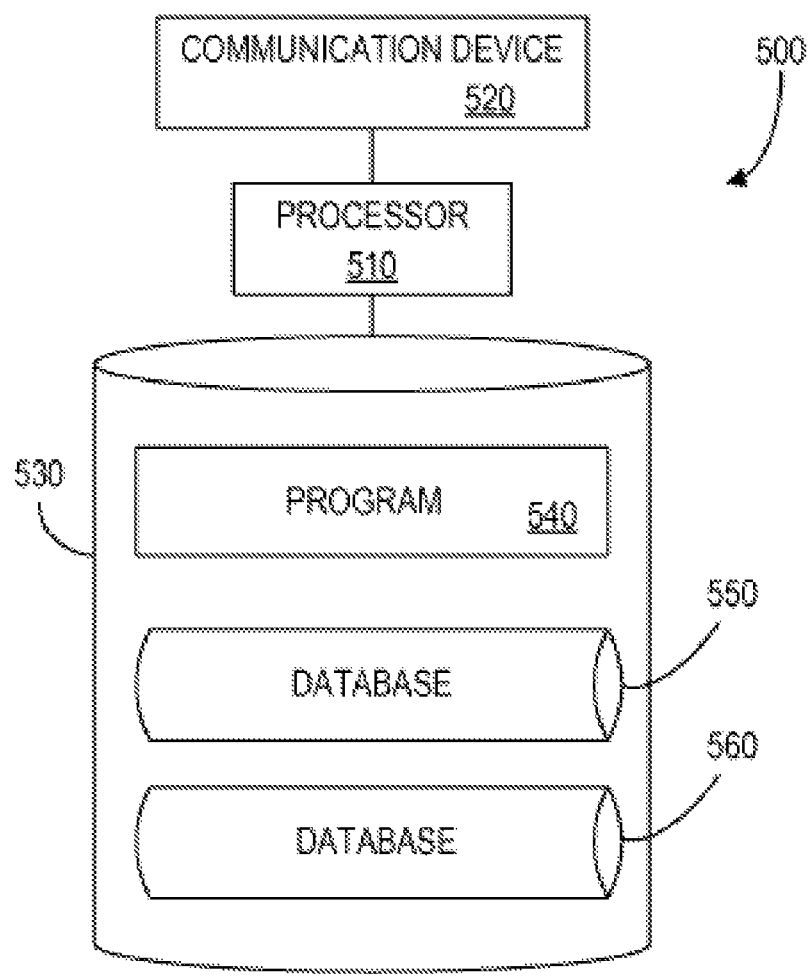
FIG. 5 is a schematic diagram of an exemplary microprocessor that may be used to implement some aspects of the present disclosure.

Referring now to FIG. 5, a schematic diagram of an exemplary micro-processor that may be used to implement some aspects of the present disclosure is illustrated. The micro-processor which can be referred to as the controller 500 can include one or more processor(s) 510, which may include one or more processor components coupled to a communication device 520. In some embodiments, a controller 500 can be used to transmit energy to the energy source placed in the ophthalmic lens and for the dispensing of the one or more active agents.

In some embodiments, the processor(s) 510 can be coupled to a communication device 520 configured to communicate energy via a communication channel. The communication device may be used to electronically communicate with components within the media insert, for example. The communication device 520 may also be used to communicate, for example, with one or more controller apparatus or programming/interface device components.

The processor 510 is also in communication with a storage device 530. The storage device 530 may include any appropriate information storage device, including combinations of magnetic storage devices, optical storage devices, and/or semiconductor memory devices such as Random Access Memory (RAM) devices and Read Only Memory (ROM) devices.

The storage device 530 can store a program 540 for controlling the processor 510. The processor 510 performs instructions of a software program 540. For example, the processor 510 may receive information descriptive of a sensed ophthalmic condition, component placement, a timer, and the like. The storage device 530 can also store ophthalmic related data in one or more databases 550 and 560. The database may include, for example, predetermined surrounding environment condition thresholds, sensed data, and specific control sequences for controlling components, e.g., controlling energy between components. The database may also include parameters and controlling algorithms for the control of the release system that may reside in the ophthalmic device as well as data and/or measured feedback that can result from their action. In some embodiments, that data may be ultimately communicated to/from an external reception device.

Figure 6:
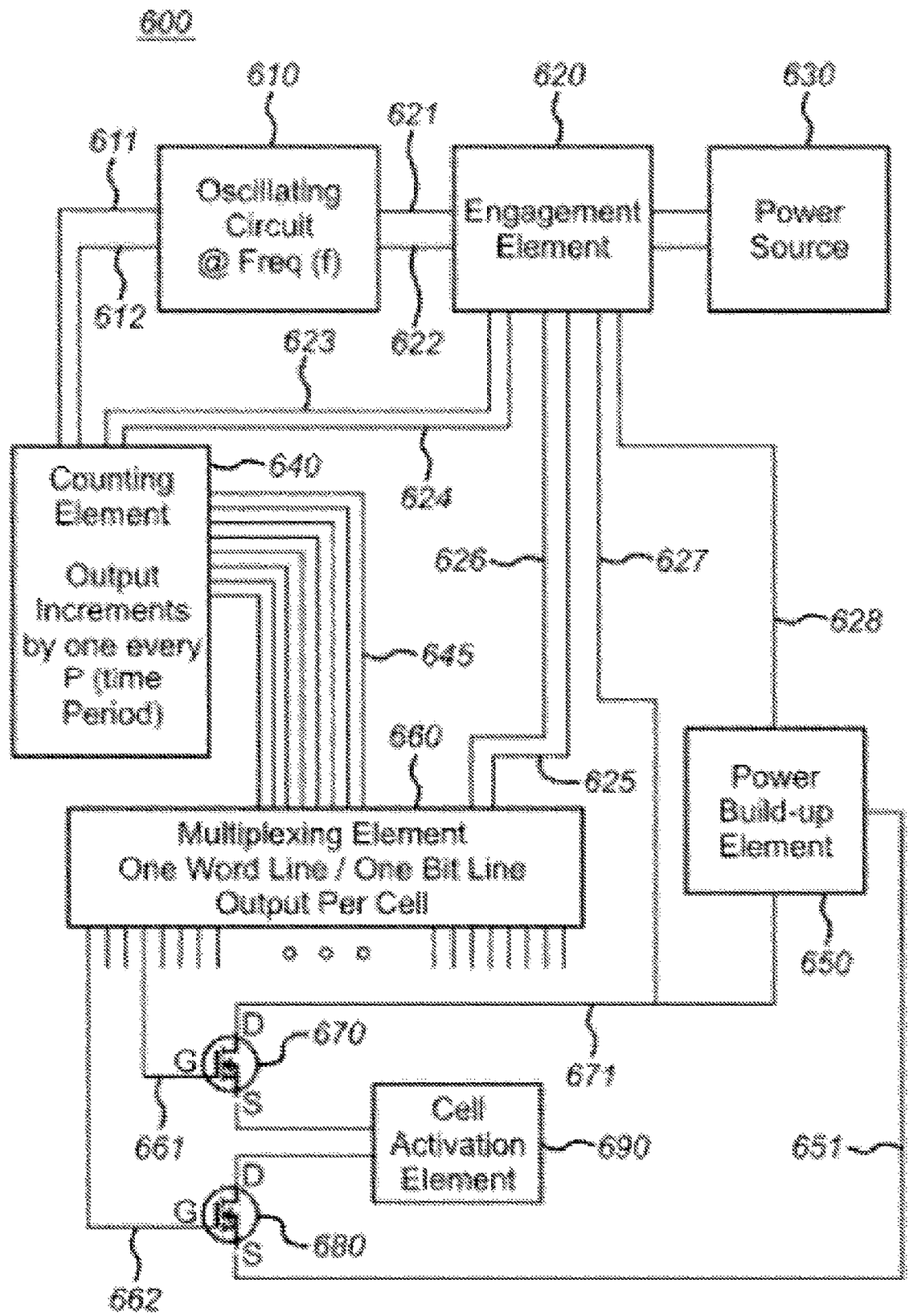
FIG. 6 illustrates an exemplary design for interconnections to individual active agent containers in a containment array.

Referring now to FIG. 6, an exemplary design 600 for interconnections to individual active agent containment cells is depicted, including timing and control circuits that can be used to activate a particular containment cell. In some embodiments, the circuit can include a power source 630. This power source may be an alkaline battery or an energy receptor (e.g., an antenna). The power may be routed from the power source to the engagement element 620. This element may be set to an "on" state when the ophthalmic device is placed into the eye environment. When it is set to an on state, then the power source may be routed through engagement element 620 and out to other circuit elements. Items 621 and 622 may be the routing to an oscillating circuit element 610. Items 623 and 624 may be the routing to a counting element 640. Items 625 and 626 may be the routing to a multiplexing element 660. And, items 627 and 628 may be the routing to a power build-up element 650.

Once the power is engaged in the energized ophthalmic device, the oscillating circuit may begin its oscillation at a particular frequency. The output of element 610 may be passed to the counting element 640 via items 611 and 612. The counting element 640 may have a duty cycle that counts for a certain number of cycles on the input line 612. In an exemplary sense, the combination of the frequency of oscillation and the count required before the output of the counting element increments by one may correspond to a specified time period (e.g., 2 hours). Therefore, in this example, every two hours the output of counting element 640 will be increased by one count. This count may be encoded into an eight bit number which is passed from the counting element 640 to the multiplexing element 660 through the data bus 645.

The multiplexing element 660 may receive the eight bit number and decode this number into a unique combination of a first word line 661 and a first bit line 662. When a particular word line is activated (e.g., line 661), it may turn on a power transistor 670 to current flow. The bit line 662 may turn on a power transistor 680. As was shown in FIG. 3, a combination of bit line and word line may address a unique array element in the containment array 300. When the power transistors are engaged, power may be routed from a power build up element 650 through line 651, then through cell activation element 690, and out of line 671. When the current runs through the cell activation element, or the cell activation element is otherwise engaged, the metal cap may fold out of the way, thereby exposing the active agent contained in the respective containment cell to the surrounding environment.

There may be numerous variations that are possible with this type of circuit. For example, it may be possible to use the charge up time of item 650 in concert with a resistive element to determine the timing from one cell exposure to another replacing the need for an oscillating circuit. Other variations that may be possible include, for example, that the multiplexing element addresses a unique output line for every containment cell. In addition, the circuit may activate a single cell at a particular time period. It may be apparent to one skilled in the art that various diversity may derive from electronically controlled delivery; including in a non-limiting sense delivering discrete doses of active agent from containment cells at different programmed rates, and programming multiple containment cells to deliver doses at a particular time period.

Figure 7:
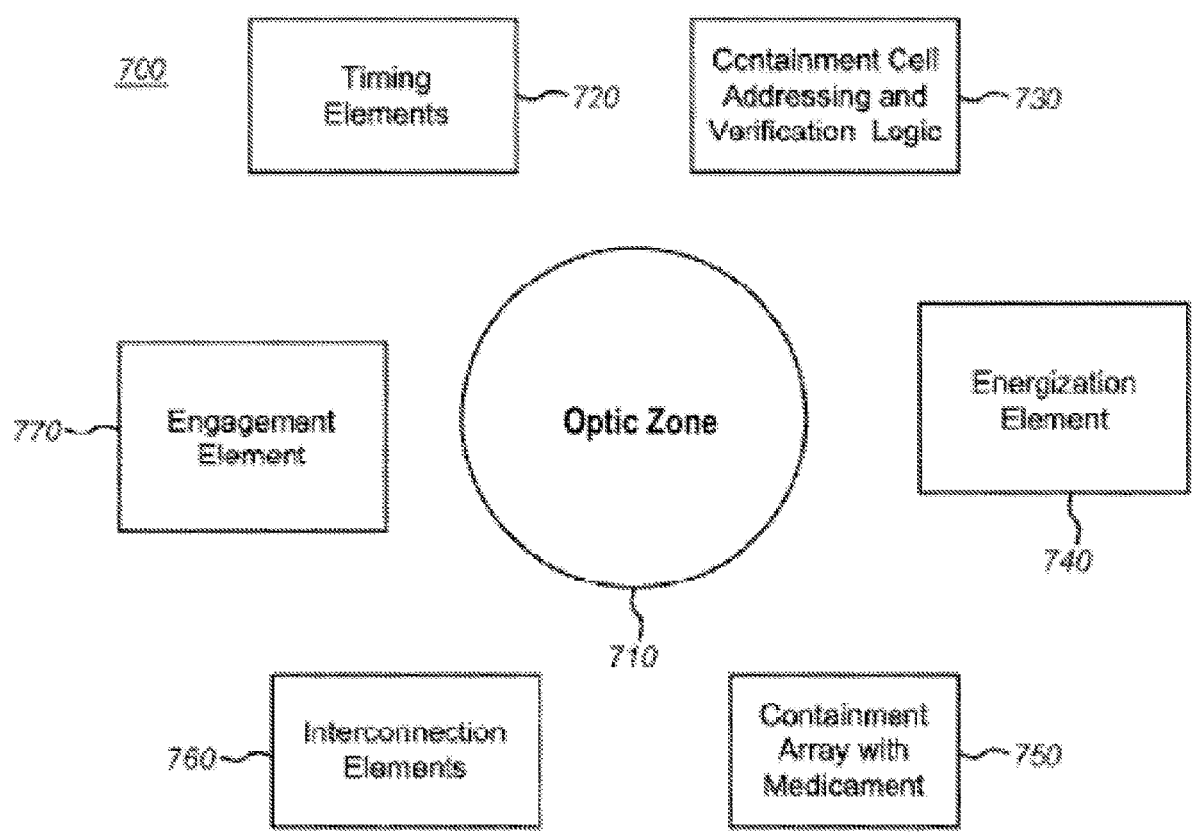
FIG. 7 illustrates a block diagram of an ophthalmic device with an energized containment array.

Referring now to FIG. 7, a block diagram showing components of an exemplary ophthalmic device with an energized containment array is depicted. In particular, and as mentioned in the previous paragraphs, the formed energized ophthalmic device may contain all of the elements shown at 700 as items optic zone 710, timing elements 720, containment cell addressing and verification logic 730, energization element 740, containment array 750 with medicament, interconnection elements 760, and activation or engagement element 770. It may be instructive to consider how these elements may function in practice.

An ophthalmic device may be placed on the anterior surface of the eye. In the process of placing the ophthalmic device in the eye the engagement element 770 may be set to an "on" state. This can allow for power to be sent from an energization element 740, to all the other elements. The timing elements 720 (e.g., oscillator and counting elements), may begin to start counting. After a preprogrammed time has elapsed, e.g., two hours, the counting element may index a position. The verification logic 730 may then configure a single word line and a single bit line to conduct current. This combination will define an array element within the containment array 750 and the current flow may cause the metal cap to fold, thereby uncovering the active agent of this first containment cell. In some embodiments, opening of the containment cell may allow for tear fluid to enter the cell and dissolve a dissolvable active agent away. Accordingly, the active agent may be quickly released into the eye environment in a well-regulated manner. A second counter may also be used, for example, to disengage the multiplexer after a certain count has been reached, so that the battery element is not discharged should a failure cause a constant current draw.

Figure 8:
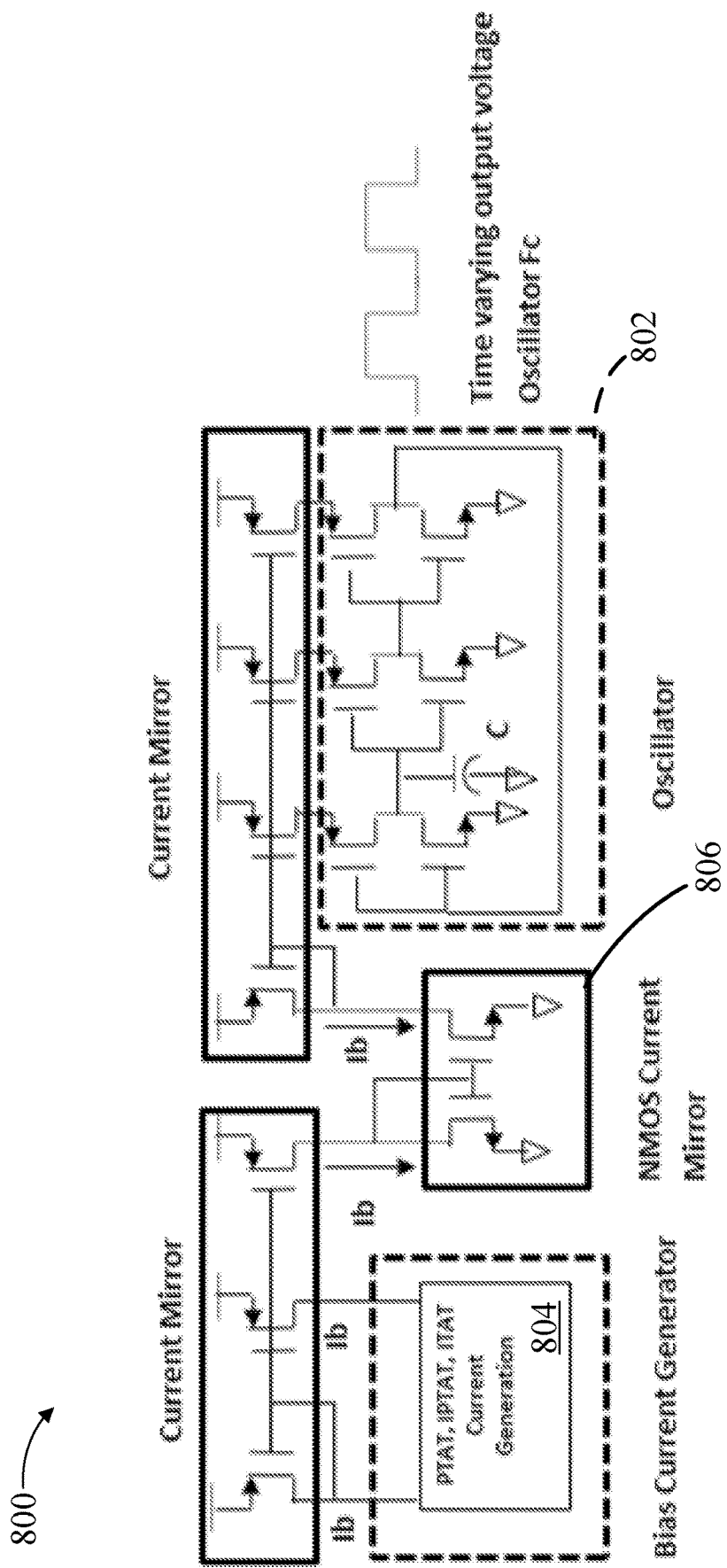
FIG. 8 is a schematic block diagram of an exemplary timer circuit or time reference block in accordance with aspects of the present disclosure.

Timing elements (e.g., timing elements 720 (FIG. 7)) may be or comprise a time reference block or a timer circuit 800, such as illustrated in FIG. 8. The timer circuit 800 may be configured as a long period timer (e.g., on the order of 24 hours) and may be low power (e.g., <5 nA, <4 nA, <3 nA of quiescent current) during the period. As an example, the timer circuit 800 may be configured on or in an ophthalmic device or other ocular drug delivery device that may be located in the Caruncula or other region of the eye. As a further example, the various systems described herein may make use of the timer circuit 800. However, other systems and device may benefit from the timer circuit 800.

The timer circuit 800 may comprise a time varying signal to act as a reference such that a voltage or current signal can be counted and timing calculated to a required set point. In certain aspects, a crystal oscillator may be used for timer applications such as these. However, existing quartz (crystal) oscillators are not typically manufactured in this low frequency range. Additionally or alternatively, crystal oscillators are not available with the quiescent current consumption (e.g., <5 nA, <4 nA, <3 nA of quiescent current) as typically a series of buffers is needed to generate a signal useful for timing and counting. Moreover, conventional crystal oscillators may not be integrated into dimensions suitable for a contact lens or ocular drug delivery system. As such, the timer circuit 800 may comprise an integrated current controlled oscillator 802 as a time reference for the circuit 800.

The timer circuit 800 may be integrated in a standard CMOS process using a current bias generator 804 and the oscillator 802 having an output frequency that depends on a bias current (Ib) and capacitance C. The bias current may be generated with any practical implementation. Typical configurations include Proportional to Absolute Temperature (PTAT), Inversely Proportional to Absolute Temperature (IPTAT) and Independent of Absolute Temperature (ITAT). There are several configurations of oscillators which use current and capacitance to set a frequency. The configuration depicted in FIG. 8 is a so-called current-starved ring oscillator. The timer circuit 800 provides a time based voltage signal that changes state at a fundamental frequency/time period which can be counted and measured.

Due to practical limits of the CMOS process such as leakage current, parasitic capacitance and the limited capacitance and resistance per unit area, the bias current and capacitance may not be practically sized to achieve a 24 hour time period using the bias current generator 804 and oscillator 802 stage alone. In order to achieve the required time period, for example, the fundamental frequency of the oscillator 802 may be lowered using a series of frequency dividers. The frequency division can be scaled such that the fundamental frequency of the oscillator 802 is extended to cover a period that includes the desired 24 hour time or other extended time period. The frequency division can be implemented with any practical CMOS divider circuit. As an example, the frequency division may be implemented using a classic integer-n division. D Flip Flops (DFF) are arranged in a ripple counter 900 configuration (FIG. 9) or divide by 2. The current consumption of the frequency divider may be managed by use of the ripple counter 900, which may allow control of the current consumption of the frequency divider by optimizing the current consumption of the DFF. The DFF may comprise PMOS and NMOS transistors connected in inverter and tri-state inverter configurations. As an example, when the inverter switches, the PMOS transistor and NMOS transistor may be activated (e.g., temporarily). When the PMOS and NMOS transistors are both activated, the positive voltage supply (Vpositive) may be momentarily connected to ground through the series connection of the on-resistance of the PMOS transistor (RonPMOS) and the on resistance of the NMOS transistor (RonNMOS). The current that momentarily flows (Iinverter) is governed by ohm's law where Iinverter=Vpositive/(RonPMOS+RonNMOS). RonPMOS and RonNMOS can be increased by increasing the gate length of the PMOS and NMOS transistors. The gate length increase lowers the current and acts to slow the speed of the DFF down. The gate increase must be balanced versus the required speed of the DFF. DFFs that reside further down the chain in the ripple counter have very low speed requirements such that switching current optimization is straight forward. Changing the NMOS and PMOS device sizes also allows internal signal delays of the DFF to be optimized. Signals can be timed such that the NMOS and PMOS transistors are not allowed to turn on at the same time. This optimization is referred to as make before break timing. As described in the previous example, the current consumption may be optimized by preventing large currents to transition from the positive supply to ground during switching, such as in the inverter stages of the Flip Flop. Such a current limit may be controlled by optimizing the device size and some make before break timing on the switches. The period of the timer may be programmed by selecting the desired frequency tap.

One contributor to current consumption in certain circuits described herein may be the static current consumed in the bias current generator. For example, as the reference current is scaled lower, the variation increases. The variation may increase to a point where the current is not useful as a bias for the oscillator 802 (FIG. 8). In order to further lower the quiescent current of the reference current, timer circuits such as the timer circuit 800 (FIG. 8) may be configured to turn a quiescent current, of the bias current generator 804, for example, on and off with predetermined duty cycle generated by an oscillator circuit (e.g., oscillator 802) and a divider network (e.g., ripple counter 900 (FIG. 9)). The ripple counter comprises flip-flops 902.

Figure 9:
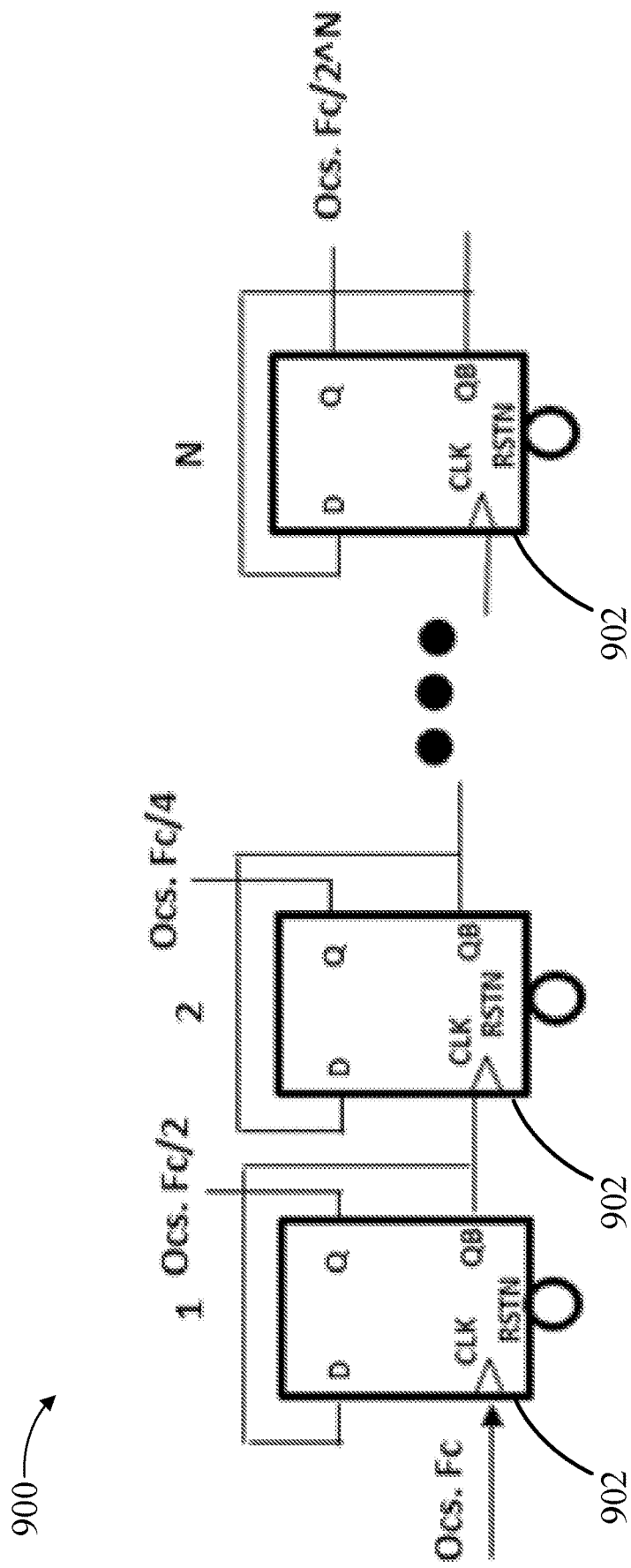
FIG. 9 is a schematic block diagram of an exemplary ripple counter in accordance with aspects of the present disclosure.
Figure 10:
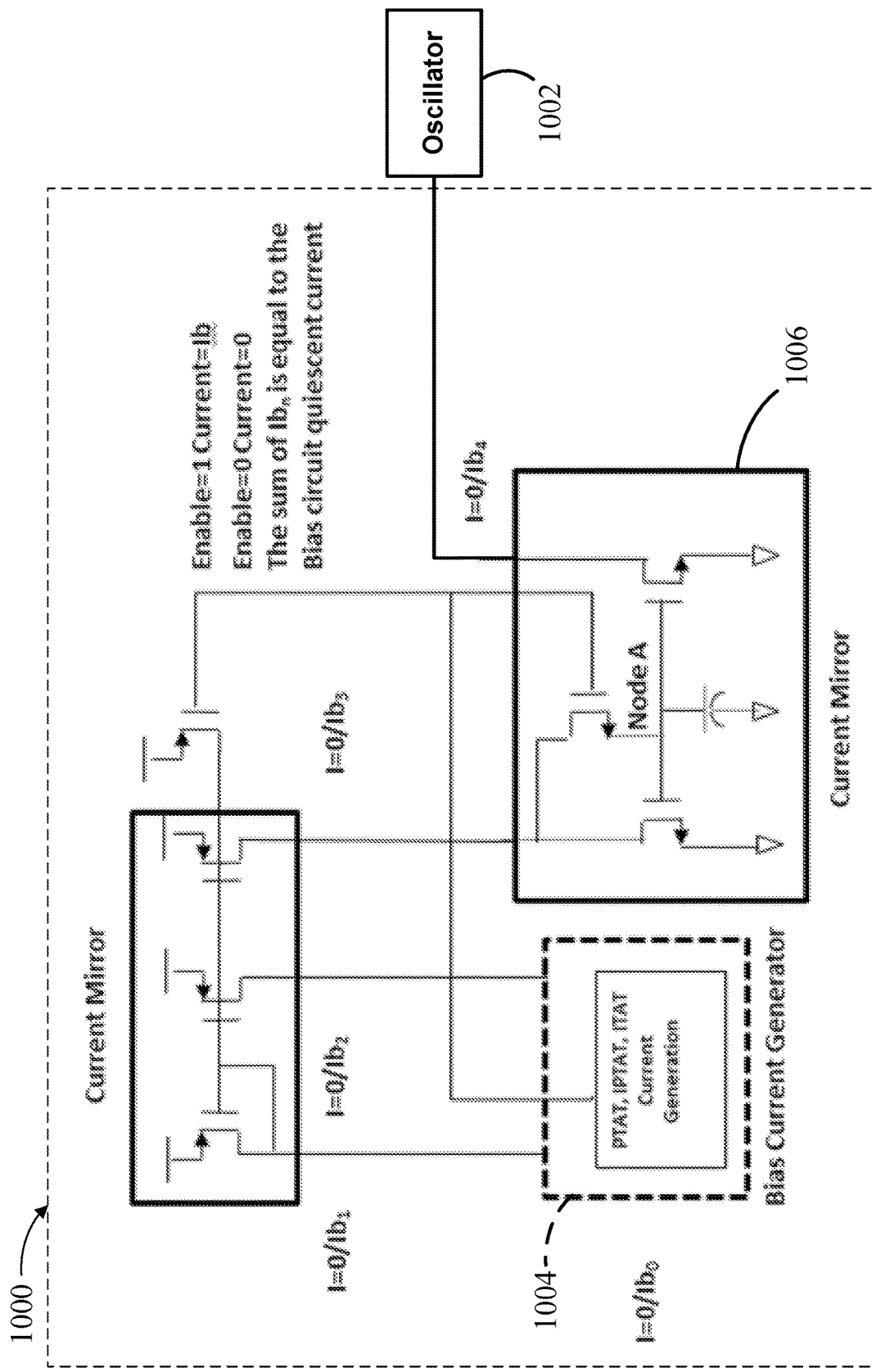
FIG. 10 is a schematic block diagram of an exemplary bias current duty cycle generation circuit in accordance with aspects of the present disclosure.

Referring to FIG. 10, the duty cycle may be implemented by a reference timer (reference block) such as timer circuit 1000, which may be similar to the timer circuit 800 except as described herein. In certain aspects, the timer circuit 1000 may comprise or be in communication with an oscillator 1002. The timer circuit 1000 may comprise a bias current generator 1004, and one or more current mirrors such as NMOS current mirror 1006. The oscillator 1002 and bias current generator 1004 may be similar to the oscillator 802 and bias current generator 804, except as described herein. For example, the bias current generator 1004 may comprise enable switches 1008 and the NMOS current mirror 1006 may comprise a sampling capacitor 1010 and sampling switch 1012. In certain embodiments, the signals that control the enable switches and/or sampling switches may be developed from DFF divider networks such as the ripple counter 900 (FIG. 9). For example, when the bias current generator 1004 is disabled the sampling capacitor 1010 on the NMOS current mirror 1006 may be configured to maintain the gate voltage of the mirror 1006 and thus the bias current in the oscillator 802. The sampling capacitor 1010 may have a leakage component that causes the sampled voltage to slowly lower (e.g., droop). The voltage droop may change the bias current of the oscillator 1002, which in turn changes the frequency of the oscillator 1002. The gate voltage on the mirror 1062 may be refreshed before the oscillator frequency variability increases beyond a pre-determined limit.

Figure 11:
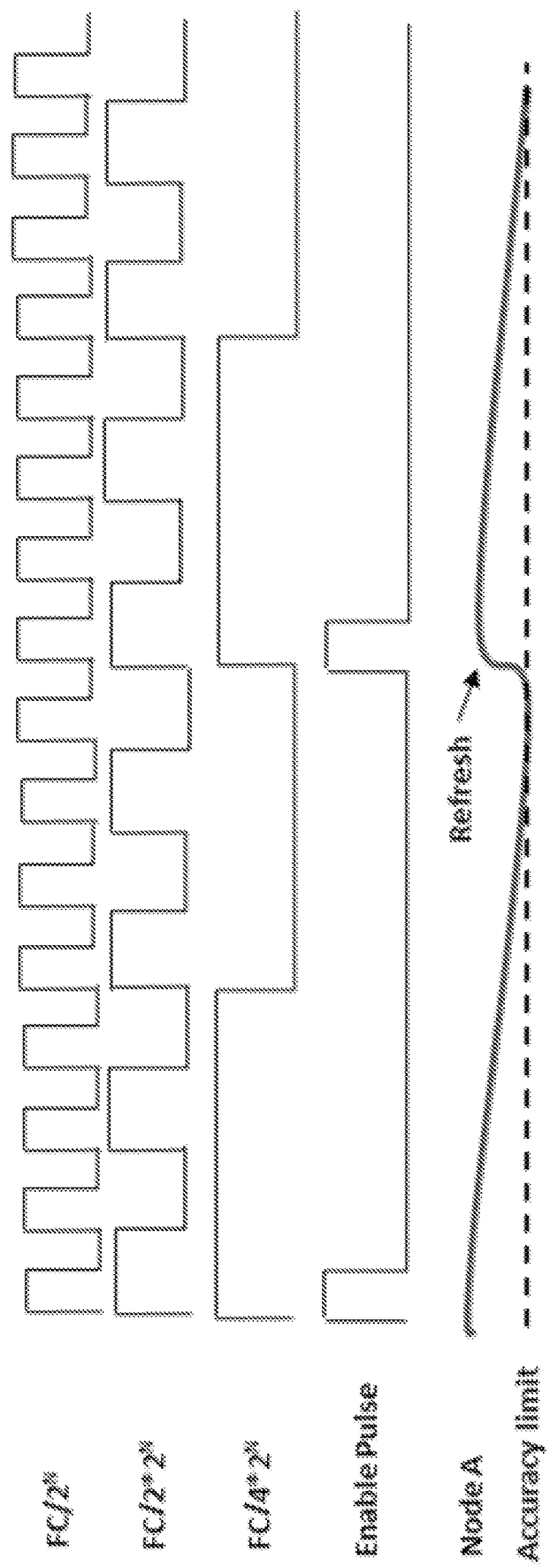
FIG. 11 is a graphical plot of exemplary pulses in accordance with aspects of the present disclosure.

The reduction in quiescent current may be implemented as described below. Once the oscillator (e.g., oscillator 1002) starts up, frequencies may be available at Fc (the fundamental frequency of the oscillator) Fc/2, Fc/4 F and up to $Fc/2^N$ where N is the number of divider stages. By combining the clocks, a pulse of variable length may be generated depending on the clocks used. The pulse may be used as the enable signal for the bias circuit. When enable is high, the quiescent current may be at its normal bias level. When the enable signal is low, the quiescent current may be at zero (0). The effective bias quiescent current may be lowered by the ratio of the time the enable signal is high to the time the enable signal is low. The amount of time the bias current can remain low may be determined by the accuracy limits of the oscillator 1002, such as oscillator 1002. When enable is low leakage lowers the voltage at node A (FIG. 10). As this voltage lowers the bias current to the oscillator 1002 lowers and the frequency begins to change. The voltage at node A may be "refreshed" before it droops lower than the required accuracy limit. As an illustrative example, FIG. 11 shows the signals and timing to generate a 1/16 ratio and related lowering of the quiescent bias current. However, other ratios not shown in FIG. 11 are possible.

In order to allow the oscillator 1002 and/or timer circuit 1000 to startup properly, the enable signal may start with the quiescent current on. This initial state may be accomplished by resetting an integer-n divider circuit (e.g., ripple counter 900) using the output of the oscillator 1002. As such, the output of the oscillator 1002 may begin low and may be used to hold RSTN of the DFF divider network low. RSTN holds the Q terminal of the DFF low and the QB terminal (inverted Q terminal) of the DFF high. When the oscillator 1002 makes its first transition to a high state the DFF chain, in the ripple counter 900, for example, is taken out of reset and allowed to function. This reset may be latched such that the falling edge of the oscillator does not reset the divider network The appropriate QB terminal may be used as the enable signal such that it starts high and after an initial period goes low and periodically repeats. For example, a reference enable pulse generation circuit may use a DFF with combinational circuitry to generate the enable pulse for the reference. As such, the Q terminal of the DFF used for pulse generation will be low when held in reset. The QB terminal of the DFF used for pulse generation will be high when held in reset. The QB terminal may be chosen to generate the reference enable signal so that the reference will start out enabled during reset. This condition allows the oscillator 1002 to be initially functioning. The oscillator 1002 may then transition from a low to a high output and enable the DFF divider chain (e.g., ripple counter 900). The DFF divider chain will in turn cause the pulse generation circuit Q to transition from low to high which will change the QB signal which is the reference enable from high to low. When the reference enable is low the quiescent current is reduced. This action is repeated every pulse generation period such that the reference is briefly enabled and refreshed. Such a startup configuration allows the bias current generator 1004 to be initially enabled, which allows the oscillator 1002 to start up. Once the oscillator 1002 starts up, the core quiescent current of the bias current generator 1004 may be lowered to zero for some predetermined period of time throughout the period of oscillation. The allowed zero time period may be determined by the allowed variation of the oscillator fundamental frequency, which in turn may be determined by the leakage of the sampling capacitor in the mirror 1006. The zero current time period lowers the effective average quiescent current of the bias current generator 1004 below the limit imposed by the variation.

Figure 12:
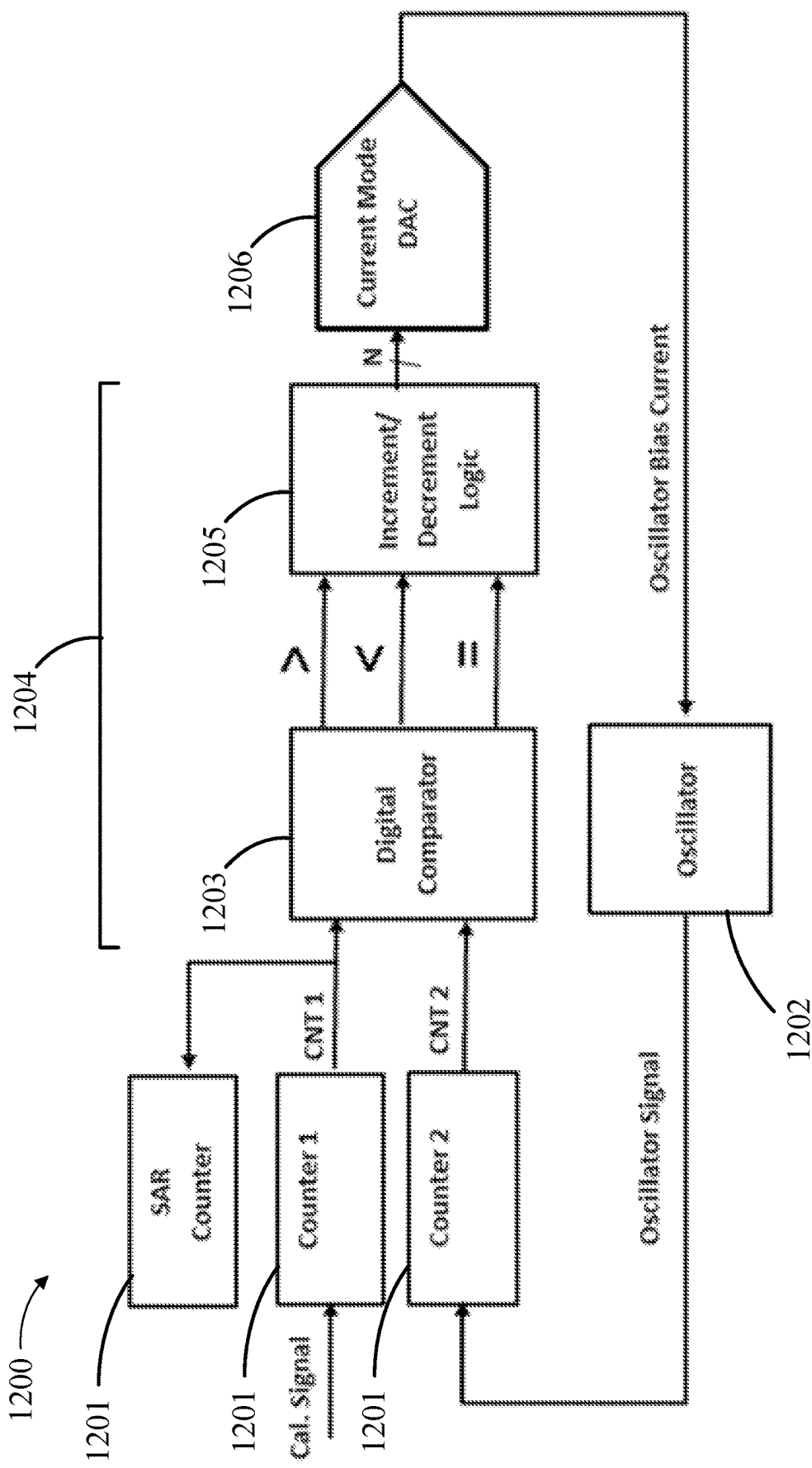
FIG. 12 is a schematic block diagram of an exemplary frequency trim circuit in accordance with aspects of the present disclosure

Due to at least the component tolerance limitations, the accuracy of the frequency may not meet the requirements of certain timer application. In order to address such accuracy requirements, a frequency trim circuit 1200 (FIG. 12) may be added to the circuitry such as the timer circuit 1000. As illustrated in FIG. 12, the frequency trim circuit 1200 operates to synch the oscillator frequency to an input reference frequency (calibration signal). This calibration signal can be applied to the timer circuit in any practical manner. Two example applications of the calibration frequency are at the start of the timer period or during testing of the IC.

One possible trim method for the timer circuit may be implemented using a Successive Approximation technique. For example, the circuitry is implemented with digital counters 1201, a digital comparator combinational logic 1204, and a current mode Digital-to Analog Converter (DAC) 1206. The digital counters 1201 may comprise a Successive Approximation Routine (SAR) counter configured to receive an output of one or more other counters. Alternatively or additionally, the one or more other counters may be configured to receive a calibration signal. The calibration signal may have a known pulse width and period and may be generated externally from the frequency trim circuit 1200 and/or the overall timer circuit. The calibration signal may be received from a microprocessor or wireless communication. The trim circuit 1200 may be configured to alter the onboard oscillator pulse width and period to match the calibration signal pulse width and period.

The digital comparator combinational logic 1204 may comprise a digital comparator 1203 configured to receive the output of at least two of the counters 1201 and analyze (e.g., compare) the received outputs. The digital comparator combinational logic 1204 may comprise an increment/decrement logic 1205 configured to receive an output of the digital comparator 1203 and to cause an output (e.g., N) to increment or decrement based at least on the received output of the digital comparator 1203. The number of bits in the DAC 1206 may determine the number of steps in the Successive Approximation Routine (N) and the accuracy of the trim (accuracy in $\%=100\times\frac{1}{2}^N$). The DAC 1206 may be configured to adjust the bias current transmitted to an oscillator 1202 (e.g., oscillator 1002 (FIG. 10)), which in turn raises and lowers the oscillation frequency. An example, trim process may include one or more of the following operations:

1. Time (T)=0, The calibration frequency is input to Counter 1 which performs a fixed count of the positive pulses of the calibration signal (in this case a count of a power of 2 is the easiest count to implement).
2. At T=0 the Oscillator signal is applied to counter 2.
3. At T=0 the DAC code is set to full scale/2 (FS/2).
4. At T=0 the SAR counter count=0 (SARCNT).
5. Counter 1 reaches the fixed count it freezes the count of Counter 2, resets Counter 1 and increments the SAR counter.
6. The output count of Counter2 (CNT2) is compared to Counter 1 (CNT1).
7. If CNT2<CNT1 set DAC code to FS/2+(FS/(2*2$^N$)) full scale, where N is the step.
8. If CNT2>CNT1 set DAC code to FS/2−(FS/(2*2$^N$)) full scale, where N is the step.
9. If CNT2=CNT1 freeze DAC code, stop frequency trim. A range can also be used for this comparison (e.g. CNT1−1<CNT2<CNT1+1)
10. If SARCNT<N then repeat steps 1-6 w/ the new DAC code setting.
11. If SARCNT>N then stop frequency trim.

Figure 13:
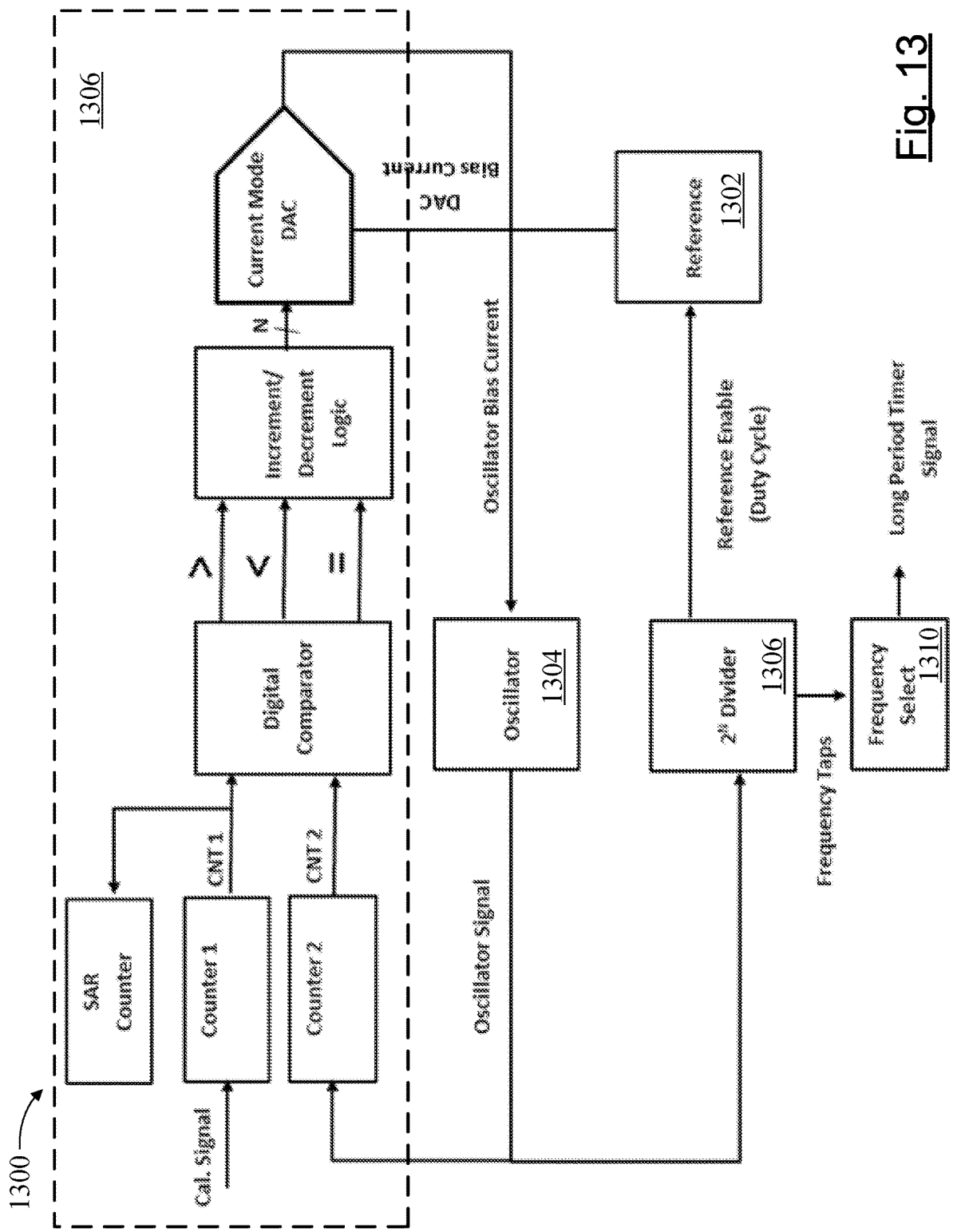
FIG. 13 is a schematic block diagram of an exemplary timer circuit or time reference block in accordance with aspects of the present disclosure.

By using the method defined above, the frequency trim circuit 1200 performs a binary search for N steps and sets the oscillator frequency to the same value as the calibration frequency within the resolution of the DAC 1206. However, other frequency trim methods may be used. Once the frequency is calibrated the DAC setting can be locked in by One Time Programmable (OTP) memory circuitry or EEPROM. Various combinations of circuits described herein may be used to achieve a programmable timer that may be operated over periods on the order of 24 hours, while consuming <5 nA of current. As an example, FIG. 13 illustrates a timer circuit 1300 comprising a reference block 1302 (e.g., timer circuit 800 (FIG. 8), timer circuit 1000 (FIG. 10), etc.) an oscillator 1304, a frequency divider such as 2$^N$ divider 1306 (e.g., ripple counter 900 (FIG. 9), a frequency trim circuit 1308 (e.g., circuit 1200 (FIG. 12), and a frequency select block 1310. It is understood that the various circuits and components described herein may be incorporated in various configurations, such as illustrated in FIG. 13 to provide a timer signal that may be referenced over periods on the order of 24 hours, while consuming less than 5 nA of current over the time period. Other configurations may be used.

As shown in FIG. 13, a power-on reset function may combined with a reference enable such that the reference block 1302 is disabled until power-on reset goes high. The oscillator 1304 may be initialized such that its output is low when the reference block 1302 is disabled, thus holding the $2^N$ divider circuit 1306 off during reset. The power-on reset transitions from low to high enabling the reference block 1302, which in turn starts the oscillator 1304. When the oscillator 1304 transitions from low to high the $2^N$ divider 1306 begins counting. The reference enable periodically goes low per the timing of the pulse generation. The output of the reference block 1302 is held by a sampling capacitor such that the oscillator 1304 is operational, but its frequency begins to drift. The reference enable is brought high periodically resetting the oscillator 1304 frequency to its original value. If the oscillation frequency is not within desired limits, trim (calibration) can be implemented. Trim begins when a calibration signal is applied to counter 1 of the frequency trim circuit 1308. The trim algorithm executes as described in the example trim process above. At the end of the calibration, the oscillator frequency is trimmed to the desired frequency and the reference block 1302 is enabled and disabled according to the adjusted timing implemented in the reference enable pulse generation circuitry. As such, the frequency select block 1310 may be configured to tap a desired frequency and allow a timer signal to be outputted for reference by a device, system, or circuit as a timing reference. Such a timing reference may be made available over a period of time such as 24 hours, while minimizing current usage such as quiescent current of less than 5 nA. As an example the timer circuit 1300 may be implemented as a timing reference for a drug delivery system, as described herein. As a further example, the timer circuit 1300 may be implemented as a timing reference an indication or alarm system configured to provide an alert/alarm to a user at a given time. Such alerts/alarms may be audible, visual, haptic, or a combination thereof. Other systems, devices, and components may make use of the timer circuits described herein. Moreover, the timer circuits may be programmed to provide a particular timer signal frequency depending on the need of the system referencing the timer signal.

Many features and advantages of the disclosure are apparent from the detailed specification, and thus, it is intended by the appended claims to cover all such features and advantages of the disclosure which fall within the true spirit and scope of the disclosure. Further, because numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

What is claimed is:

1. A programmable timer circuit comprising:
    a reference circuit configured to generate a bias current;
    a current controlled oscillator configured to receive the bias current; and
    a frequency divider network configured to divide an output of the oscillator, wherein the circuit is capable of generating a timer signal for a pre-determined period, while using less than 5 nA of quiescent current, and wherein the timer signal is based on the divided output of the oscillator; and
    a frequency trim circuit configured to control a characteristic of the oscillator and/or the bias current received by the oscillator; wherein the frequency trim circuit is configured to receive a calibration signal and to control the characteristic of the oscillator and/or the bias current received by the oscillator based at least on the calibration signal; and wherein the frequency trim circuit is configured to implement a Successive Approximation technique implemented via:
        a first digital counter comprising a Successive Approximate Routine counter configured to receive an output of a second digital counter and a calibration signal having a known pulse width and period;
        a digital comparator combinational logic; and
        a current mode Digital-to Analog Converter.

2. The programmable timer circuit of claim 1, wherein the reference circuit comprises a bias current generator and a current mirror configured to generate the bias current.

3. The programmable timer circuit of claim 1, wherein the bias current is generated based at least on the divided output of the oscillator.

4. The programmable timer circuit of claim 1, wherein the frequency divider network comprises a ripple counter.

5. The programmable timer circuit of claim 4, wherein the ripple counter is configured as an integer-N divide by 2 frequency divider.

6. The programmable timer circuit of claim 1, wherein the timer signal is generated at one or more select frequencies throughout the pre-determined period of time.

7. An ophthalmic device comprising the circuit of claim 1.

8. The ophthalmic device of claim 7, wherein the ophthalmic device comprises a contact lens, an intraocular lens, an overlay lens, an ocular insert, or an optical insert, or a punctal plug, or a combination thereof.

9. The ophthalmic device of claim 7, further comprising one or more containment cells, wherein at least one of the one or more containment cells contains an active agent, and wherein the at least one of the one or more containment cells is configured to release the active agent in response to an output of the timer signal.

10. The ophthalmic device of claim 7, wherein the active agent can include one or more of: a lubricant, a saline, a solvent, a vitamin, an antimicrobial, an antifungal, and a medicament.

11. The ophthalmic device of claim 7, wherein an alarm is triggered in response to at least the timer signal.

12. The ophthalmic device of claim 11, wherein the alarm is one or more of audible, optical, and haptic.

* * * * *